United States Patent
Masaki et al.

(10) Patent No.: US 10,441,141 B2
(45) Date of Patent: Oct. 15, 2019

(54) DRIVE SHAFT, INSERTION INSTRUMENT AND INSERTION DEVICE

(71) Applicant: OLYMPUS CORPORATION, Tokyo (JP)

(72) Inventors: Yutaka Masaki, Mitaka (JP); Kimihiko Naito, Kawasaki (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 15/481,956

(22) Filed: Apr. 7, 2017

(65) Prior Publication Data
US 2017/0209026 A1 Jul. 27, 2017

Related U.S. Application Data

(63) Continuation of application No. PCT/JP2016/059913, filed on Mar. 28, 2016.

(30) Foreign Application Priority Data

Jun. 18, 2015 (JP) .................... 2015-122970

(51) Int. Cl.
A61B 1/005 (2006.01)
A61B 1/00 (2006.01)
(Continued)

(52) U.S. Cl.
CPC ...... *A61B 1/00133* (2013.01); *A61B 1/00009* (2013.01); *A61B 1/0016* (2013.01);
(Continued)

(58) Field of Classification Search
CPC ............ A61B 1/00133; A61B 17/1631; A61B 1/00156; B08B 9/045; E03C 1/302; E03F 9/005
(Continued)

(56) References Cited

U.S. PATENT DOCUMENTS 1,963,561 A * 6/1934 Sanger .................... E03C 1/302
15/104.33
2,244,735 A * 6/1941 Silverman ............. B08B 9/0436
15/104.33
(Continued)

FOREIGN PATENT DOCUMENTS

CN 1846599 A 10/2006
JP 2006-288433 A 10/2006
(Continued)

OTHER PUBLICATIONS

International Search Report dated Jun. 21, 2016 issued in PCT/JP2016/059913.
(Continued)

*Primary Examiner* — Andrew M Tecco
*Assistant Examiner* — Eyamindae C Jallow
(74) *Attorney, Agent, or Firm* — Scully Scott Murphy & Presser, P.C.

(57) ABSTRACT

A drive shaft extends inside a tubular section along a shaft axis, and the drive shaft rotates around the shaft axis while transmitting a driving force generated in a driving source to a driven portion. The drive shaft includes multiple extension sections, and a hard section. Each of the extension sections extends along the shaft axis. The hard section is interposed between two of the extension sections in a direction along the shaft axis, and has a higher rigidity in comparison to that of the extension sections.

11 Claims, 3 Drawing Sheets

(51) Int. Cl.
*A61B 1/018* (2006.01)
*A61B 1/05* (2006.01)

(52) U.S. Cl.
CPC .............. *A61B 1/018* (2013.01); *A61B 1/051* (2013.01); *A61B 1/00135* (2013.01)

(58) Field of Classification Search
USPC ................................................ 606/114, 137
See application file for complete search history.

(56) References Cited

U.S. PATENT DOCUMENTS

| | | | | |
|---|---|---|---|---|
| 3,121,244 | A * | 2/1964 | Hunt ........................ | E03C 1/302 15/104.33 |
| 3,457,580 | A * | 7/1969 | Meyers ..................... | F28G 3/12 15/104.33 |
| 4,926,518 | A * | 5/1990 | Mikol ...................... | E03C 1/302 15/104.33 |
| 2007/0093840 | A1* | 4/2007 | Pacelli ................ | A61B 17/1631 606/80 |
| 2009/0023994 | A1 | 1/2009 | Kura et al. | |
| 2009/0143642 | A1* | 6/2009 | Takahashi .......... | A61B 1/00147 600/106 |
| 2009/0171152 | A1 | 7/2009 | Aoki et al. | |
| 2009/0209812 | A1 | 8/2009 | Omoto | |
| 2009/0233747 | A1 | 9/2009 | Sheridan et al. | |
| 2010/0063357 | A1* | 3/2010 | Watanabe .......... | A61B 1/00154 600/114 |
| 2010/0217072 | A1* | 8/2010 | Kondoh ............. | A61B 1/00071 600/101 |
| 2011/0182656 | A1* | 7/2011 | Babb ...................... | B08B 9/043 403/265 |
| 2012/0029476 | A1* | 2/2012 | Kanazawa ............ | A61M 25/09 604/528 |
| 2012/0041421 | A1* | 2/2012 | Nishigishi ............. | A61M 25/09 604/528 |
| 2014/0296771 | A1 | 10/2014 | Naito | |
| 2014/0298932 | A1 | 10/2014 | Okamoto | |
| 2018/0369883 | A1* | 12/2018 | Kehoe ..................... | E03C 1/302 |

FOREIGN PATENT DOCUMENTS

| | | |
|---|---|---|
| JP | 2009-189653 A | 8/2009 |
| JP | 2011-517967 A | 6/2011 |
| JP | 5617056 B2 | 10/2014 |
| WO | 2007/013211 A1 | 2/2007 |
| WO | WO 2013/038720 A1 | 3/2013 |
| WO | WO 2015/019675 A1 | 2/2015 |

OTHER PUBLICATIONS

English translation of International Preliminary Report on Patentability dated Dec. 28, 2017 together with the Written Opinion received in related International Application No. PCT/JP2016/059913.
Chinese Office Action dated Jun. 4, 2018 in Chinese Patent Application No. 201680003345.X.
Anonymous, "Welle (Mechanik)—Wikipedia", Jun. 1, 2015, Retrieved from the Internet URL: https://de.wikipedia.org/w/index.php?title=Welle_(Mechanik)&oldid=142687091 [retrieved on Feb. 27, 2019].
Extended Supplementary European Search Report dated Mar. 7, 2019 in European Patent Application No. 16 81 1277.9.
Chinese Office Action dated Apr. 23, 2019 in Chinese Patent Application No. 201680003345.X.

* cited by examiner

DRIVE SHAFT, INSERTION INSTRUMENT AND INSERTION DEVICE

CROSS-REFERENCE TO RELATED APPLICATIONS

This is a Continuation application of PCT Application No. PCT/JP2016/059913, filed Mar. 28, 2016 and based upon and claiming the benefit of priority from prior Japanese Patent Application No. 2015-122970, filed Jun. 18, 2015, the entire contents of which are incorporated herein by reference.

BACKGROUND OF THE INVENTION

1. Field of the Invention

The present invention generally relates to a drive shaft that rotates around a shaft axis when transmitting a driving force from a driving source to a driven portion. It also relates to an insertion instrument including such a drive shaft, and an insertion device including such an insertion instrument.

2. Description of the Related Art

International Publication No. 2013/038720 discloses an endoscopic device including an insertion section that extends along the longitudinal axis, and an assistance tool (spiral unit) attached to the insertion section. In this endoscopic device, a drive shaft extends inside the insertion section (tubular section). When a motor (driving source) provided in a held section (operation section) of the endoscope generates a driving force, the drive shaft is rotated around the shaft axis by the driving force transmitted to the drive shaft. When the drive shaft rotates, the driving force is transmitted to a rotor (driven portion) provided in the insertion section, and rotates the rotor around the longitudinal axis. When the rotor rotates in a state that the assistance tool is attached to the insertion section, the assistance tool rotates together with the rotor around the longitudinal axis.

BRIEF SUMMARY OF THE INVENTION

According to one aspect of the invention, a drive shaft which extends along a shaft axis inside a tubular section, and which is configured to rotate around the shaft axis while transmitting a driving force generated in a driving source to a driven portion, the drive shaft including: a plurality of extension sections each of which extends along the shaft axis; and a hard section which is interposed between two of the extension sections in a direction along the shaft axis, and which has a higher rigidity in comparison to the extension sections.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

Figure 1:
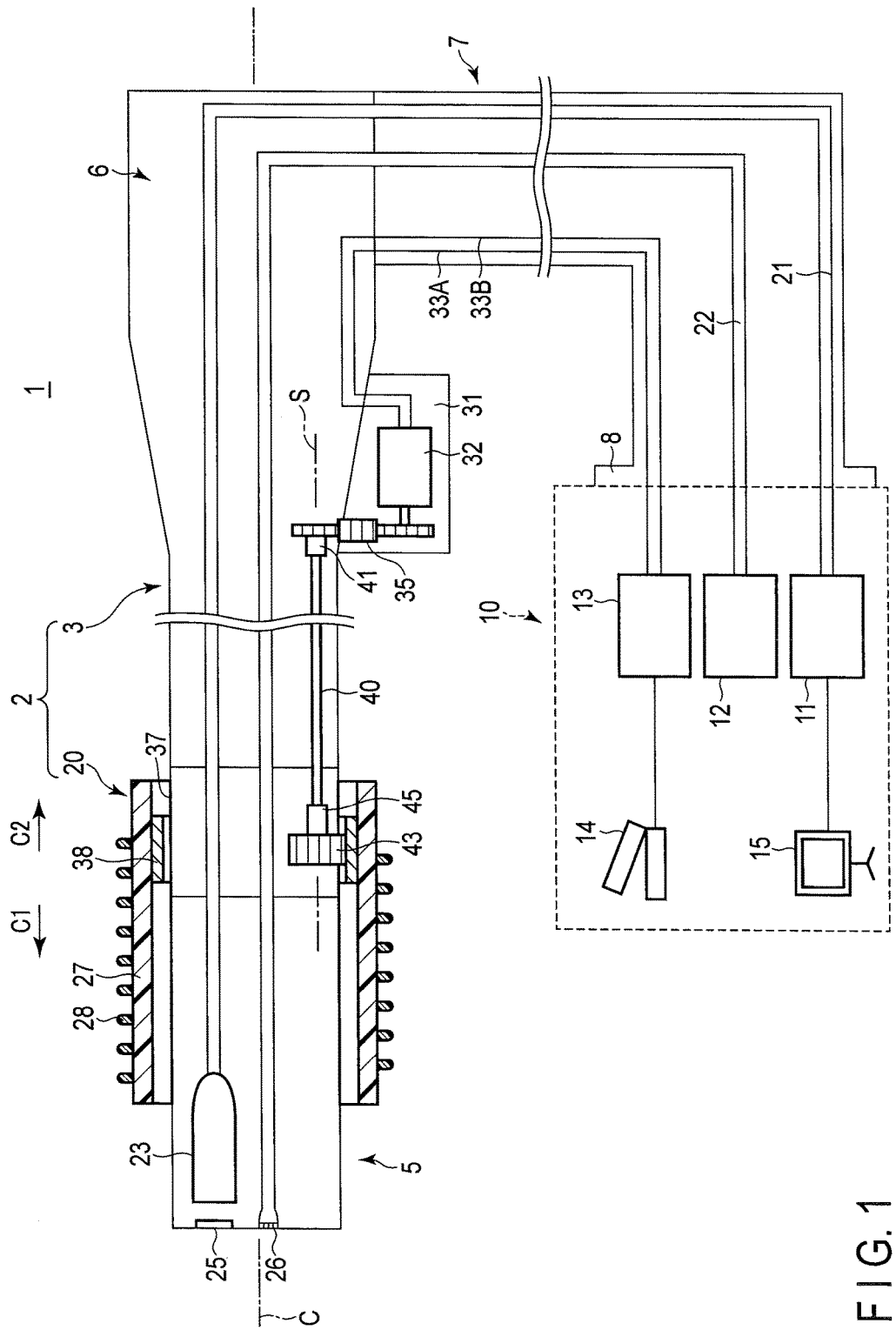
FIG. 1 is a schematic diagram showing an endoscopic system which adopts an endoscopic device according to the first embodiment.

The first embodiment of the present invention will be explained with reference to FIGS. 1 to 3. FIG. 1 is a diagram showing an endoscopic system 1 including an endoscopic device 2, which serves as an insertion device of this embodiment.

As illustrated in FIG. 1, the endoscopic device 2 includes an endoscope 3 which serves as an insertion instrument, and a spiral unit 20 which serves as an assistance tool. The endoscope 3 includes an insertion section 5, and the insertion section 5 has a longitudinal axis C. The direction along the longitudinal axis C is defined as a longitudinal direction. One side of the longitudinal direction is the distal side (the side indicated by arrow C1 in FIG. 1), and the side opposite to the distal side is the proximal side (the side indicated by arrow C2 in FIG. 1). The insertion section 5 extends from the proximal side to the distal side along the longitudinal axis C. An operation section 6 is provided on the proximal side of the insertion section 5 in the endoscope 3. The endoscope 3 is also provided with a universal cord 7, one end of which is connected to the operation section 6. In the other end of the universal cord 7, a scope connector 8 is provided.

The endoscopic system 1 includes, as a peripheral devices unit 10, an image processing device 11 such as an image processor, a light source device 12 such as a lamp, a drive control device 13, an operation input device 14 such as a foot switch, and a display device 15 such as a monitor. The universal cord 7 is detachably connected to the peripheral devices unit 10 by the scope connector 8. In the endoscope 3, an imaging cable 21 and a light guide 22 extend through inside the insertion section 5, the operation section 6, and the universal cord 7. An imaging element 23, such as CCD is arranged inside the distal portion of the insertion section 5. The imaging element 23 captures an image of a subject through an observation window 25 provided on the outer surface of the distal portion of the insertion section 5. Thereafter, an image signal is transmitted to an image processing device 11 by way of an imaging cable 21, where the image processing is performed. In this manner, the image processing device 11 creates an image of the subject, and the created image of the subject is displayed on the display device 15. The light emitted from the light source device 12 is guided through the light guide 22. Then, the subject is irradiated with the guided light through the irradiation window 26 provided on the outer surface of the distal portion of the insertion section 5.

In the endoscopic device 2, the spiral unit 20 is detachably attached to the insertion section 5 in such a manner that the insertion section 5 is inserted through the spiral unit (assistance tool) 20. The spiral unit 20 is substantially coaxial to the insertion section 5, while the spiral unit 20 is attached to the insertion section 5. The spiral unit 20 includes a cylindrical tubular main body 27 that extends along the longitudinal axis C, and a spiral fin 28 that protrudes toward outer peripheral side from the outer peripheral surface of the tubular main body 27. The spiral fin 28 extends spirally around the longitudinal axis C. The spiral unit (assistance tool) 20 is rotatable around the longitudinal axis C.

In the endoscope 3, a motor casing 31 is attached to the operation section 6. An electric motor 32, which serves as a driving source, is provided inside the motor casing 31. The electric motor 32 is provided on the proximal side with respect to the insertion section 5. One end of each of electric wirings 33A and 33B is connected to the electric motor 32. The electric wirings 33A and 33B run through inside the operation section 6 and the universal cord 7, and are connected to the drive control device 13. The drive control device 13 controls the driving electric power supplied to the electric motor 32 based on the operation input by the operation input device 14, thereby controlling the driving state of the electric motor 32. The drive control device 13 is provided with a processor or an integrated circuit including such as a central processing unit (CPU) or application specific integrated circuit (ASIC), and a storage medium such as a memory. When the driving electric power is supplied to the electric motor 32, a driving force is generated. A gear train 35 is coupled to the electric motor 32.

The drive shaft 40 extends inside the insertion section 5, which is a tubular section, from the proximal side to the distal side. The drive shaft 40 extends along the shaft axis S (that is essentially parallel to the longitudinal axis C). The proximal end of the drive shaft 40 is connected to the gear train 35 via a proximal side connecting member (driving source side connecting member) 41.

The insertion section 5 includes a base 37, and a rotor (driven portion) 38 attached to the base 37 rotatably around the longitudinal axis C with respect to the base 37. The spiral unit (assistance tool) 20 is attached to the insertion section 5 in such a manner as to cover the outer peripheral sides of the base 37 and the rotor 38. A drive gear 43 is attached to the base 37. The inner peripheral surface of the rotor 38 is engaged with the drive gear 43, and thereby the drive gear 43 is connected to the rotor 38. The distal end of the drive shaft 40 is connected to the drive gear 43 via a distal side connecting member (driven portion side connecting member) 45.

The driving force is generated by the electric motor (driving source) 32, and the generated driving force is transmitted to the drive shaft 40 by way of the gear train 35. As a result, the drive shaft 40 rotates around the shaft axis S, thereby transmitting the driving force from the proximal side (driving source side) to the distal side (driven portion side). With the driving force conveyed from the drive shaft 40 to the rotor 38 by way of the drive gear 43, the rotor (driven portion) 38 is driven and rotates around the longitudinal axis C with respect to the base 37. When the rotor 38 is driven while the spiral unit 20 is attached to the insertion section 5, a driving force is conveyed from the rotor (driven portion) 38 to the spiral unit (assistance tool) 20. With such an arrangement, the spiral unit 20 rotates together with the rotor 38 around the longitudinal axis C with respect to the base 37. According to the present embodiment, when the spiral unit 20 rotates while a pressing force acts upon the spiral fin 28 toward inner peripheral side, a propulsion force toward the distal side or proximal side is exerted upon the insertion section 5 and the spiral unit 20.

Figure 2:
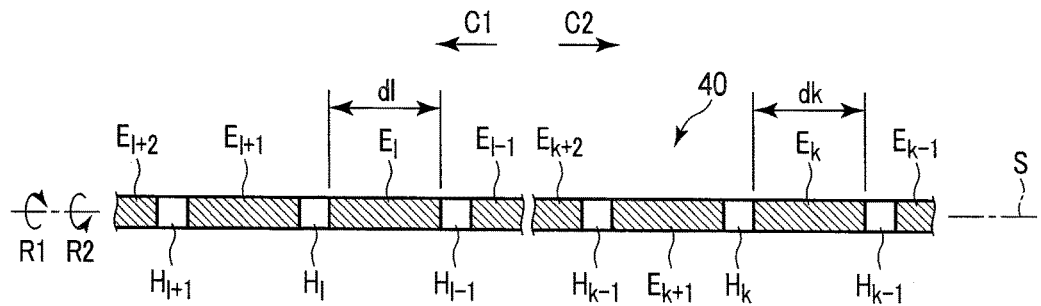
FIG. 2 is a schematic diagram showing a drive shaft according to the first embodiment.
Figure 3:
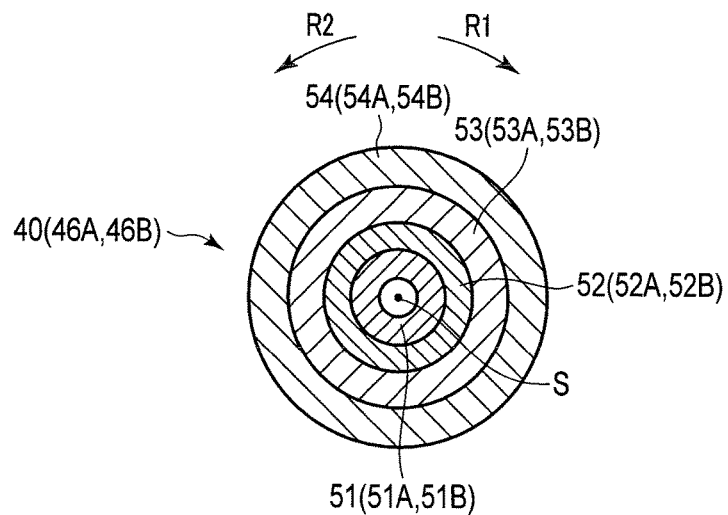
FIG. 3 is a sectional view schematically showing the drive shaft according to the first embodiment in a section perpendicular to the shaft axis.

FIG. 2 shows the configuration of the drive shaft 40, and FIG. 3 shows the drive shaft 40 in section perpendicular to the shaft axis S. As illustrated in FIGS. 2 and 3, the drive shaft 40 includes multiple coil layers (four coil layers according to the present embodiment) 51-54. In the drive shaft 40, the coil layer 51, coil layer 52, coil layer 53, and coil layer 54 are deposited in this order from the inner periphery side to the outer periphery side, and the coil layer 54 forms the outermost layer of the drive shaft 40. Each of the coil layers 51-54 is formed spirally around the shaft axis S. It is preferable that each of the coil layers 51-54 is wound in a direction opposite to the winding direction of its adjacent coil layer/layers (corresponding one or two of 51-54) in the radial direction of the drive shaft 40. For example, the coil layers 52 and 54 may be formed in spiral shapes which extend toward one side (indicated by the arrow R1 in FIGS. 2 and 3) around the shaft axis S as extending from the proximal side (driving source side) to the distal side (driven portion side), whereas the coil layers 51 and 53 may be formed in spiral shapes which extend toward the other side (indicated by the arrow R2 in FIGS. 2 and 3) around the shaft axis S as extending from the proximal side to the distal side.

In the drive shaft 40, multiple extension sections Ei (i=1, 2, . . . , k, . . . , l, . . . , n, n+1) and hard sections (multiple hard sections according to the present embodiment) Hi (i=1, 2, . . . , k, . . . , l, . . . , n) extend along the shaft axis S. The hard section Hi is formed by brazing the entire periphery of the outer peripheral surface of the outermost coil layer 54. No brazing is conducted for any of the extension sections Ei, and the extension sections Ei are formed with the coil layers 51-54 only. For this reason, the hard section Hi becomes harder than the extension sections Ei, providing a rigid body with a higher rigidity in comparison to that of the extension sections Ei. The extension sections Ei provide an elastic body with a higher elasticity (flexibility) in comparison to that of the hard section Hi.

Each hard section Hi is provided between corresponding two extension sections (corresponding two of Ei) in a direction along the shaft axis S. For example, the hard section Hk is provided between the extension section Ek and extension section Ek+1. In the drive shaft 40, the extension sections Ei and hard sections Hi are alternately arranged in line, from the proximal side (driving source side) to the distal side (driven portion side). As a result, the hard sections Hi having a high rigidity are formed between the proximal end (driving source-side end) and distal end (driven portion-side end) in the drive shaft 40. Between the hard section Hi and its adjacent hard sections (corresponding one or two of Hi) in the direction along the shaft axis S, corresponding one or two extension section/sections (corresponding one or two of Ei). Thus, the hard sections Hi are arranged in such a manner as to be spaced apart from each other in the direction along the shaft axis S.

According to the present embodiment, the hard sections Hi are arranged approximately at equal intervals in the direction along the shaft axis S over the entire length of the drive shaft 40 from its proximal to distal ends. In other words, when a spacing distance di (i=1, 2, . . . , k, . . . , l, . . . , n) between one hard section Hi and its adjacent hard section/sections (corresponding one or two of Hi) in the direction along the shaft axis S is defined, all the spacing distances di become approximately the same. For instance, the spacing distance dk between the hard section Hk−1 and hard section Hk becomes approximately the same as the spacing distance dl between the hard section Hl−1 and the hard section Hl.

Next, the function and advantageous effects offered by the drive shaft 40 and the endoscopic device 2 according to the present embodiment are explained. When a lumen is under observation using an endoscopic system 1 (endoscopic device 2), the spiral unit (assistance tool) 20 is attached to the insertion section 5, and the insertion section 5 and the spiral unit 20 are inserted into the lumen such as an intestine lumen. Thereafter, the electric motor 32 is driven in accordance with the operation input by the operation input device 14, and the driving force is transmitted to the spiral unit 20, as described above. With such an arrangement, the spiral unit 20 rotates around the longitudinal axis (revolving axis) C. The spiral unit 20 rotates under the pressure exerted on the spiral fin 28 toward inner peripheral side against the wall of the lumen so that a propulsion force to the distal side or proximal side (in one side of direction along the longitudinal axis C) is exerted on the insertion section 5 and the spiral unit 20. This propulsion force enhances the mobility of the insertion section 5 inside the lumen.

As discussed above, the drive shaft 40 includes multiple coil layers 51-54, each of which is spirally formed around the shaft axis S. With such an arrangement, when the drive shaft 40 rotates around the shaft axis S, thereby transmitting the driving force from the proximal side (driving source side) to the distal side (driven portion side) in the drive shaft 40, twisting occurs in the drive shaft 40. According to the present embodiment, the hard sections Hi having a high rigidity are arranged between the proximal end (driving source-side end) and distal end (driven portion-side end) in the drive shaft 40. Even when a torque produced on the drive shaft 40 increases while the drive shaft 40 is conveying the driving force, twisting does not occur in the hard sections Hi. Since the hard sections Hi where twisting does not occur are arranged, the twist amount is reduced in each of the extension sections Ei, even if the torque produced on the drive shaft increases. This prevents the twist amount from increasing in the drive shaft 40 when the drive shaft 40 is transmitting the driving force from the proximal side to the distal side.

When the drive shaft 40 is rotating around the shaft axis S, twisting occurs in the drive shaft 40, which makes the drive shaft 40 expand or contract in a direction parallel to the shaft axis S. For instance, the drive shaft contracts when the drive shaft 40 rotates toward one side (in a direction indicated by arrow R1 in FIGS. 2 and 3) around the shaft axis S. The drive shaft 40 expands when the drive shaft 40 rotates toward the other side around the shaft axis S (in a direction indicated by arrow R2 in FIGS. 2 and 3). As discussed above, since the drive shaft 40 is provided with the hard sections Hi according to the present embodiment, the twist amount is reduced in the drive shaft 40 (each of the extension sections Ei) even when the torque produced on the drive shaft 40 increases. With the twist amount of the drive shaft 40 reduced, the expansion amount and contraction amount of the drive shaft 40 can be reduced, even when the torque produced on the drive shaft 40, while is transmitting the driving force, increases. Thus, the drive shaft 40 is effectively prevented from being significantly expanded or contracted when the drive shaft 40 is transmitting the driving force.

According to the present embodiment, as discussed above, the twist amount, expansion amount, and contraction amount of the drive shaft 40 can be kept low during the rotation of the drive shaft 40. In this manner, the efficiency of transmitting the driving force from the driving source side to the driven portion can be ensured.

In addition, the drive shaft 40 is provided with the extension sections Ei having a high elasticity (flexibility). This arrangement ensures the flexibility of the drive shaft 40, even with the hard sections Hi arranged therein. Thus, the flexibility of the insertion section 5 can be ensured in the part of the insertion section 5 corresponding to where the drive shaft 40 extends inside (the portion of the insertion section 5 on the proximal side with respect to the base 37).

The hard sections Hi are arranged approximately at equal intervals in the direction along the shaft axis S. With this arrangement, the twisting stress caused by the twisting during the rotation of the drive shaft 40 becomes essentially uniform in all of the extension sections Ei. As a result, while the drive shaft 40 is transmitting the driving force from the proximal side (driving source side) to the distal side (driven portion side), the twisting stress is applied to the drive shaft 40 essentially evenly over its entire length in the direction along the shaft axis S.

Modifications of First Embodiment

Figure 4:
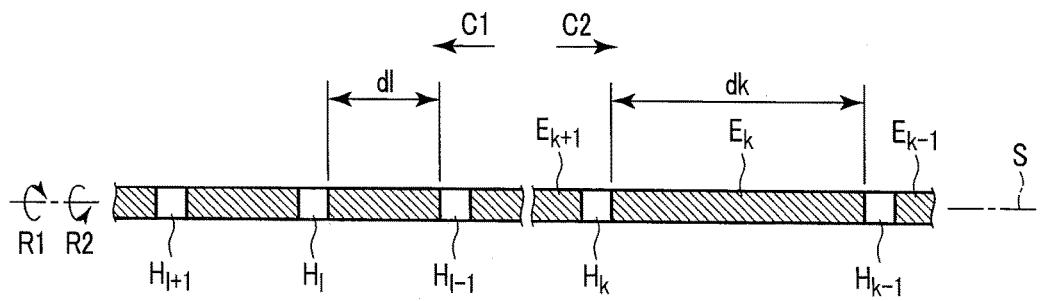
FIG. 4 is a schematic diagram showing a drive shaft according to the first modification of the first embodiment.

In the first modification of the first embodiment illustrated in FIG. 4, the drive shaft 40 includes intervals between the hard sections Hi in the direction along the shaft axis S that are set smaller in the portion on the distal side (driven portion side) in comparison to the portion on the proximal side (driving source side). In particular, in the drive shaft 40 of this modification, the spacing distance di between one hard section Hi and its adjacent hard section/sections (corresponding one or two of Hi) along the shaft axis S is smaller in the portion on the distal side (driven portion side) in comparison to the portion on the proximal side (driving source side). For instance, the spacing distance dl between the hard section Hl−1 and the hard section H1 is smaller than the spacing distance dk between the hard section Hk−1 and the hard section Hk. As a result, the hard sections Hi are arranged more closely to each other, and have a higher rigidity in the portion on the distal side of the drive shaft 40 in comparison to the portion on the proximal side.

When the drive shaft 40 is rotating around the shaft axis S, a larger load is applied to a portion of the drive shaft 40 that is closer to the rotor 38 serving as a driven portion. In this modification, with the above arrangement of the hard sections Hi, the rigidity can be ensured in the part of the drive shaft 40 to which a large load is applied.

Figure 5:
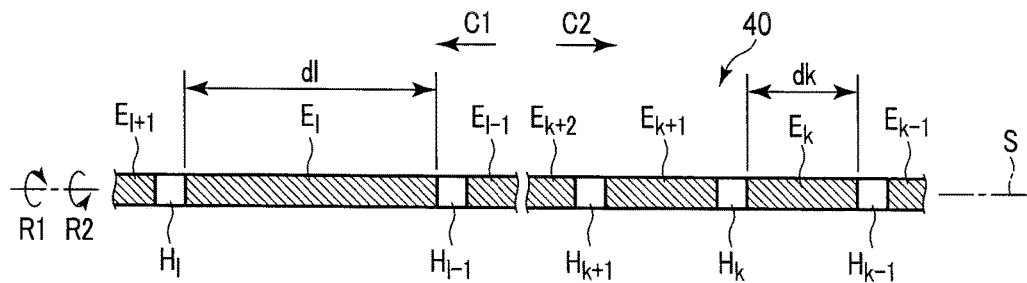
FIG. 5 is a schematic diagram showing a drive shaft according to the second modification of the first embodiment.

In the second modification of the first embodiment illustrated in FIG. 5, the intervals of the hard sections Hi in the direction along the shaft axis S are smaller in the portion on the proximal side (driving source side) in comparison to the portion on the distal side (driven portion). In particular, in the drive shaft 40 of this modification, the spacing distance di between one hard section Hi and its adjacent hard section/sections (corresponding one or two of Hi) along the shaft axis S is smaller in the proximal side (driving source side) in comparison to the distal side (driven portion side). For instance, the spacing distance dk between the hard section Hk−1 and the hard section Hk is smaller than the spacing distance dl between the hard section Hl−1 and the hard section Hl. As a result, the hard sections Hi are arranged more closely to each other and have a higher rigidity in the portion on the proximal side of the drive shaft 40 in comparison to the portion on the distal side.

In the portion of the insertion section 5 on its proximal side with respect to the base 37, it is preferable from the aspect of insertability to the lumen or the like that the flexibility decreases from the distal side to the proximal side. In this modification, the structure in which the flexibility decreases from the distal side to the proximal side in the portion of the insertion section 5 on the proximal side with respect to the base 37 can be readily realized by arranging the hard sections Hi in the manner as discussed above.

It also should be noted that the number of hard sections Hi is not definitely determined. A modification may be such that only one hard section Hi (H1) is provided in the drive shaft 40. In other words, at least one hard section (Hi) may be provided between the proximal end (driving source-side end) and dismal end (driven portion-side end) in the drive shaft 40 in such a manner that each of the hard sections Hi is interposed between corresponding two extension sections (corresponding two of Ei) in the direction along the shaft axis S.

The number of coil layers (51-54) that constitute the drive shaft 40 is also not definitely determined. In some modification, the drive shaft 40 may be constituted by a single coil layer (54). If this is the case, at least one hard section Hi may be formed in the drive shaft 40, for example, by brazing the entire peripheral of the outer peripheral surface of the coil layer (54).

Second Embodiment

The second embodiment of the present invention will be explained with reference to FIG. 6. The second embodiment is obtained by modifying the structure of the first embodiment in the manner indicated below. The same reference numerals are given to the same components as in the first embodiment, and the explanation of these components is omitted.

Figure 6:
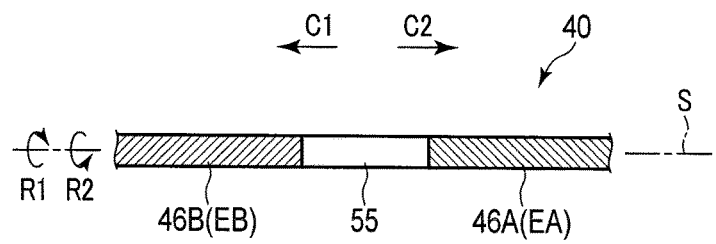
FIG. 6 is a schematic diagram showing a drive shaft according to the second embodiment.

FIG. 6 shows the configuration of the drive shaft 40. As illustrated in FIG. 6, the drive shaft 40 of the present embodiment includes a first shaft section 46A, and a second shaft section 46B arranged on the distal side (driven portion side) with respect to the first shaft section 46A. The first shaft section 46A forms an extension section (first extension section) EA that extends along the shaft axis S, and the second shaft section 46B forms an extension section (second extension section) EB that extends along the shaft axis S. The first shaft section 46A (extension section EA) is constituted by multiple coil layers (four coil layers in the present embodiment) 51A-54A, and the second shaft section 46B (extension section EB) is constituted by multiple coil layers (four coil layers in the present embodiment) 51B-54B (see FIG. 3). The coil layer (first coil layer) 54A forms the outermost layer of the first shaft section 46A. The coil layer 51A, coil layer 52A, coil layer 53A, and coil layer 54A are deposited in this order from the inner periphery side to the outer periphery side of the first shaft section 46A. The coil layer (second coil layer) 54B forms the outermost layer of the second shaft section 46B. The coil layer 51B, coil layer 52B, coil layer 53B, and coil layer 54B are deposited in this order from the inner periphery side to the outer periphery side of the second shaft section 46B.

Each of the coil layers 51A-54A and 51B-54B is formed spirally around the shaft axis S. The coil layer (first coil layer) 54A that forms the outermost layer of the first shaft section 46A (extension section EA) has a winding direction opposite to that of the coil layer (second coil layer) 54B that forms the outermost layer of the second shaft section 46B (extension section EB). For example, the coil layer 54A may be formed in a spiral shape which extends toward one side (indicated by the arrow R1 in FIG. 6) around the shaft axis S as extending from the proximal side (driving source side) to the distal side (driven portion side), whereas the coil layer 54B may be formed in a spiral shape which extends the other direction (indicated by the arrow R2 in FIG. 6) around the shaft axis S as extending from the proximal side to the distal side.

It is preferable that each of the coil layers 51A-54A is wound in a direction opposite to the winding direction of its adjacent coil layer/layers (corresponding one or two of 51A-54A) in the radial direction of the drive shaft 40, and that each of the coil layers 51B-54B is wound in a direction opposite to the winding direction of its adjacent coil layer/layers (corresponding one or two of 51B-54B) in the radial direction of the drive shaft 40. If this is the case, the coil layer 51A of the first shaft section 46A has a winding direction opposite to that of the coil layer 51B of the second shaft section 46B, and the coil layer 52A of the first shaft section 46A has a winding direction opposite to that of the coil layer 52B of the second shaft section 46B. The coil layer 53A of the first shaft section 46A has a winding direction opposite to that of the coil layer 53B of the second shaft section 46B.

A hard section 55 is interposed between the extension section (first extension section) EA of the first shaft section 46A and the extension section (second extension section) EB of the second shaft section 46B in the direction along the shaft axis S. In other words, the extension section EA is positioned adjacent to the hard section 55 on its proximal side (driving source side), and the extension section EB is positioned adjacent to the hard section 55 on its distal side (driven portion side). The coil layers 51A-54A of the first shaft section 46A are connected to the coil layers 51B-54B of the second shaft section 46B via the hard section 55.

The hard section 55 may be a pipe member formed of a metal or the like. The hard section 55 is therefore stiffer than the first shaft section 46A (extension section EA) and the second shaft section 46B (extension section EB), and is rigid body having a higher rigidity than the rigidity of the first shaft section 46A and the second shaft section 46B. The first shaft section 46A and the second shaft section 46B are elastic bodies having a higher elasticity (flexibility) in comparison to the hard section 55.

According to the present embodiment, the hard section having a high rigidity is interposed between the proximal end (driving source-side end) and the distal end (driven portion-side end) of the drive shaft 40, and therefore twisting will not occur in the hard section 55 even when a torque produced on the drive shaft 40 increases while the drive shaft 40 is transmitting the driving force. This prevents, in the same manner as in the first embodiment, the twist amount of the drive shaft 40 from increasing when the drive shaft 40 is transmitting the driving force from the proximal side to the distal side. With the twist amount of the drive shaft 40 reduced, the expansion amount and contraction amount of the drive shaft 40 can be reduced, even when a torque produced on the drive shaft 40 increases while the drive shaft 40 is transmitting the driving force.

According to the present embodiment, the coil layer 54A, which is the outermost layer of the first shaft section 46A (extension section EA), has a winding direction opposite to the coil layer 54B, which is the outermost layer of the second shaft section 46B (extension section EB). Due to such an arrangement, one of the first shaft section 46A (extension section EA) and the second shaft section 46B (extension section EB) expands, while the other one of the first shaft section 46A and the second shaft section 46B contracts, when the drive shaft 40 is rotating around the shaft axis S. For instance, the first shaft section 46A contracts and the second shaft section 46B expands when the drive shaft 40 is rotating toward one side (in a direction indicated by arrow R1 in FIG. 6) around the shaft axis S. On the other hand, the first shaft section 46A expands and the second shaft section 46B contracts when the drive shaft 40 is rotating toward the other side (in a direction indicated by arrow R2 in FIG. 6) around the shaft axis S. That is, the contraction/expansion of the first shaft section 46A is canceled out by the expansion/contraction of the second shaft section 46B. As a result, when the drive shaft 40 is rotating around the shaft axis S, the expansion amount and contraction amount of the entire drive shaft 40 in the direction along the shaft axis S can be further reduced. In this manner, the efficiency of transmitting the driving force from the driving source side to the driven portion side can be further enhanced.

Modifications of Second Embodiment

The number of coil layers (51A-54A) that constitute the first shaft section 46A and the number of coil layers (51B-54B) that constitute the second shaft section 46B are not definitely determined. In one modification, the first shaft section 46A may be constituted by a single coil layer (54A), and the second shaft section 46B may be constituted by a single coil layer (54B).

As long as the hard section 55 is interposed between the first shaft section 46A (extension section EA) and the second shaft section 46B (extension section EB) in the direction along the shaft axis S, the winding pitch of the coil layers (51A-54A) in the first shaft section 46A may differ from the winding pitch of the coil layers (51B-54B) in the second shaft section 46B. In addition, the winding pitch of the coil layers (51A-53A) of the first shaft section 46A other than the outermost layer of this section may be the same as the winding pitch of the coil layers (51B-53B) of the second shaft section 46B other than the outermost layer of this section, and the winding pitch of the outermost coil layer (54A) in the first shaft section 46A may differ from the winding pitch of the outermost coil layer (54B) of the second shaft section 46B.

As long as the hard section 55 is interposed between the first shaft section 46A and the second shaft section 46B, the diameter of the first shaft section 46A (winding diameter of the outermost coil layer (54A) of the first shaft section 46A) may differ from the diameter of the second shaft section 46B (winding diameter of the outermost coil layer (54B)). The number of coil layers (51A-54A) of the first shaft section 46A may also differ from the number of coil layers (51B-54B) of the second shaft section.

Figure 7:
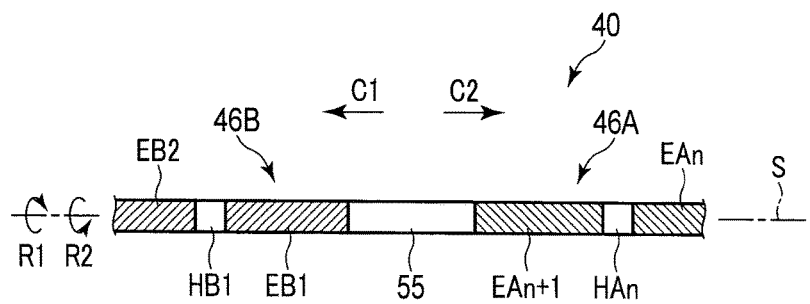
FIG. 7 is a schematic diagram showing a drive shaft according to one modification of the second embodiment.

In one modification of the second embodiment as illustrated in FIG. 7, the first shaft section 46A and the second shaft section 46B are formed in the same manner as the drive shaft 40 according to the first embodiment. In particular, in the first shaft section 46A, extension sections EAi (i=1, 2, . . . , n, n+1) and hard sections HAi (i=1, 2, . . . , n) are alternately arranged in line from the proximal side (driving source side) to the distal side (driven portion side). In the second shaft section 46B, extension sections EBi (i=1, 2, . . . , n, n+1) and hard sections HBi (i=1, 2, . . . , n) are alternately arranged in line from the proximal side to the distal side. The hard section 55 is interposed between the most distal (driven portion-side) extension section (first extension section) EAn+1 of the extension sections EAi and the most proximal (driving source-side) extension section (second extension section) EB1 of the extension sections EBi in the direction along the shaft axis S.

The hard sections HAi may be formed by brazing the entire peripheral of the outer peripheral surface of the outermost coil layer 54A of the first shaft section 46A, and the hard sections HBi may be formed by brazing the entire peripheral of the outer peripheral surface of the outermost coil layer 54B of the second shaft section 46B. As a result, the hard sections HAi, HBi, and 55 are stiffer than the extension sections EAi and EBi, providing a rigid body with a higher rigidity in comparison to that of the extension sections EAi and EBi. The extension sections EAi and EBi are elastic bodies having a higher elasticity (flexibility) in comparison to the hard sections HAi.

In this modification, in addition to the hard section 55, the hard sections HAi are provided in the first shaft section 46A, and the hard sections HBi are provided in the second shaft section 46B. In the same manner as the hard section 55, the twisting will not occur in the hard sections HAi and HBi even when a torque produced on the drive shaft 40 increases while the drive shaft 40 is transmitting the driving force. In this manner, when the drive shaft 40 is conveying the driving force from the proximal side to the distal side, the twist amount can be further reduced in the first shaft section 46A and the second shaft section 46B. As a result, the efficiency can be further enhanced in preventing the twist amount from increasing in the drive shaft 40 when the drive shaft 40 is transmitting the driving force from the proximal side to the distal side.

The hard sections HAi may or may not be arranged at equal intervals. Similarly, the hard sections HBi may or may not be arranged at equal intervals. In addition, the number of hard sections HAi and the number of hard section HBi are not definitely determined. Only one hard section HAi (HA1) may be provided in the first shaft section 46A, and only one hard section HBi (HB1) may be provided in the second shaft section 46B. In addition, the hard sections HAi may be provided in the first shaft section 46A only, while no hard section (HBi) may be provided in the second shaft section 46B. Alternatively, the hard sections HBi may be provided in the second shaft section 46B only, while no hard section (HAi) may be provided in the first shaft section 46A.

(Other Modifications)

In the above discussed embodiments, the spiral unit (20) has been described as an example of an assistance tool that is attached to the insertion section (5), but the assistance tool is not limited to the spiral unit (20) only. Furthermore, in the above discussed embodiments, the endoscope (3) has been described as an example of an insertion instrument, but the insertion instrument is not limited to the endoscope (3) only. For example, the above-described configuration may be applied to an insertion surgery system in which a manipulator is used as an insertion instrument.

Furthermore, in the above embodiments, the drive shaft (40) extends inside the insertion section (5), and the rotor 38, which serves as a driven portion, rotates when the drive shaft (40) rotates around the shaft axis (S). The configuration, however, is not limited thereto. For example, in an electrically bendable endoscope in which a pulley is provided as a driven portion inside the operation section, the configuration of the above embodiments may be applied to the drive shaft (40) that transmits the driving force to drive the pulley by rotating around the shaft axis (S). In this case, the drive shaft (40) extends inside a flexible universal cord (tubular section). When the pulley (driven portion) is driven by the driving force that is transmitted by way of the drive shaft (40), the bendable wire is pulled to bend the bending portion.

In the above embodiments, the drive shaft (40) extends inside the tubular section (5) along the shaft axis (S), and the drive shaft (40) rotates around the shaft axis (S) while transmitting the driving force generated in the driving source (32) to the driven portion (38). The drive shaft (40) includes multiple extension sections (Ei; EA, EB; EAi, EBi), and hard sections (Hi; 55; HAi, HBi, 55) interposed between two extension sections (corresponding two of Ei; EA, EB; corresponding two of EAi and EBi) in the direction along the shaft axis (S) and having a higher rigidity in comparison to that of the extension sections (Ei; EA, EB; EAi, EBi).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A drive shaft which extends along a central axis, and which is configured to transmit a driving force to a driven portion by being rotated around the central axis by a driving source, the drive shaft comprising:
   a coil-layer extension which includes one or more coil layers, the one or more coil layers being formed spirally around the central axis and extending along the central axis from a driving source side toward a driven portion side in the coil-layer extension, the coil-layer extension including:
      a plurality of extension sections which extend along the central axis, and which are arranged in line in a direction along the central axis; and
      a hard section which connects end portions of two of the extension sections in the direction along the central axis, and which has a higher rigidity in comparison to the extension sections, an outer peripheral surface of an outermost layer of the one or more coil layers being brazed to form the hard section,
   wherein the one or more coil layers extend along the central axis over the plurality of extension sections and over the hard section.

2. The drive shaft according to claim 1, wherein the plurality of extension sections include:
   a first extension section, which is arranged adjacent to the hard section on the driving source side of the hard section, the first extension section including a first coil layer as one of the one or more of the coil layers, and
   a second extension section which is arranged adjacent to the hard section on the driven portion side of the hard section, the second extension including a second coil layer as one of the one or more of the coil layers, a winding direction of the second coil layer being opposite to that of the first coil layer.

3. The drive shaft according to claim 2, wherein the first coil layer forms an outermost layer of the first extension section, and the second coil layer forms an outermost layer of the second extension section.

4. The drive shaft according to claim 2, wherein the first coil layer is connected to the second coil layer by way of the hard section.

5. The drive shaft according to claim 1, wherein the hard section includes a plurality of hard sections spaced apart from each other in the direction along the central axis, and the plurality of hard sections are arranged at equal intervals in the direction along the central axis.

6. The drive shaft according to claim 1, wherein
   the hard section includes a plurality of hard sections spaced apart from each other in the direction along the central axis, and
   intervals of the plurality of hard sections in the direction along the central axis are smaller in a portion on the driven portion side than in a portion on the driving source side.

7. The drive shaft according to claim 1, wherein
   the hard section includes a plurality of hard sections spaced apart from each other in the direction along the central axis, and
   intervals of the plurality of hard sections in the direction along the central axis are smaller in a portion on the driving source side than in a portion on the driven portion side.

8. An insertion instrument comprising: the drive shaft according to claim 1; and an insertion section which extends along a longitudinal axis, and which forms the tubular section inside which the drive shaft extends.

9. The insertion instrument according to claim 8, further comprising the driving source which is arranged on a proximal side with respect to the insertion section, and which is configured to generate the driving force that is transmitted through the drive shaft.

10. The insertion instrument according to claim 8, wherein the insertion section includes a driven portion which is configured to be driven by the driven force transmitted through the drive shaft.

11. An insertion device comprising: the insertion instrument according to claim 10; and an assistance tool which is attached to the insertion section, and to which the driving force is configured to be transmitted from the driven portion when the driven portion attached to the insertion section is driven.

* * * * *